(12) United States Patent
Yanagiya et al.

(10) Patent No.: US 8,354,238 B2
(45) Date of Patent: Jan. 15, 2013

(54) METHOD OF IMMUNOASSAYING SPECIMEN USING AGGREGATION REACTION OF MICROPARTICLES AND ASSAY KIT

(75) Inventors: Mari Yanagiya, Ibaraki (JP); Mutsumi Tanaka, Ibaraki (JP); Mieko Kosaka, Ibaraki (JP); Masayasu Enomoto, Ibaraki (JP)

(73) Assignee: Alfresa Pharma Corporation, Osaka (JP)

( * ) Notice: Subject to any disclaimer, the term of this patent is extended or adjusted under 35 U.S.C. 154(b) by 186 days.

(21) Appl. No.: 12/746,254

(22) PCT Filed: Nov. 10, 2008

(86) PCT No.: PCT/JP2008/070830
§ 371 (c)(1),
(2), (4) Date: Jun. 4, 2010

(87) PCT Pub. No.: WO2009/072385
PCT Pub. Date: Jun. 11, 2009

(65) Prior Publication Data
US 2010/0248392 A1  Sep. 30, 2010

(30) Foreign Application Priority Data
Dec. 7, 2007  (JP) .................................. 2007-317669

(51) Int. Cl.
*G01N 33/53* (2006.01)
*G01N 33/546* (2006.01)
*G01N 33/543* (2006.01)
*A61K 39/44* (2006.01)

(52) U.S. Cl. ........ 435/7.1; 435/7.93; 436/523; 436/524; 436/533; 530/391.1

(58) Field of Classification Search .................. 436/518; 435/7.1, 7.94; 422/82.05
See application file for complete search history.

(56) References Cited

U.S. PATENT DOCUMENTS

| | | |
|---|---|---|
| 4,791,067 A | 12/1988 | Sheiman et al. |
| 5,362,655 A * | 11/1994 | Schenk et al. ............... 436/520 |
| 2003/0003602 A1 | 1/2003 | Vogt et al. |
| 2003/0082589 A1 | 5/2003 | Chan et al. |

FOREIGN PATENT DOCUMENTS

| | | |
|---|---|---|
| EP | 0918218 A2 | 11/1998 |
| JP | 11153599 A | 6/1999 |
| JP | 2001337092 A | 12/2001 |
| JP | 2002296281 A | 10/2002 |
| JP | 2004325192 A | 11/2004 |
| JP | 2005508001 T | 3/2005 |
| JP | 2005283250 A | 10/2005 |
| JP | 2006038594 A | 2/2006 |
| WO | WO 2004/077011 * | 9/2004 |

* cited by examiner

*Primary Examiner* — Shafiqul Haq
(74) *Attorney, Agent, or Firm* — The Webb Law Firm

(57) ABSTRACT

A method of assaying a sample with the use of the aggregation reaction of immunological microparticles and an assay kit. The assay is conducted by using microparticles wherein the same or an analog of the analyte and a substance that specifically binds to a substance that can specifically bind to the analyte are both bound to an insoluble carrier. Thus, it becomes possible to conveniently carry out the assay even in the case where the analyte has only a small number of specific binding sites, without especially adding a competitive substance carrying hapten bonded thereto to the reaction system so as to induce simultaneous competition of the target substance and the competitive substance.

9 Claims, 2 Drawing Sheets

METHOD OF IMMUNOASSAYING SPECIMEN USING AGGREGATION REACTION OF MICROPARTICLES AND ASSAY KIT

TECHNICAL FIELD

The present invention relates to an immunoassay using microparticles having a substance bound thereto. In particular, the present invention relates to an immunoassay of a trace constituent using an antigen-antibody reaction for use mainly in the industrial, environmental, and clinical laboratory test fields, and to a reagent kit for immunoassay.

BACKGROUND ART

In recent years, automation in various types of tests such as clinical laboratory tests and reduction in the assay time thereof have been tried. As a method of these tests, an assay utilizing an immune reaction is widely used for measurement of a substance in a biological sample. Examples of the immunoassay include many methods such as RIA, EIA, immunonephelometry, latex agglutination, colloidal gold agglutination, and immunochromatography. Among such methods, the latex agglutination and the colloidal gold agglutination are capable of measurement in a homogeneous system in which the separation or washing operation of a reaction mixture is not required, and therefore suitable for automation of determination and short-time assay. In particular, colloidal gold particles have a size of 5 nm to 100 nm, which is smaller than the size of latex particles, so that colloidal gold particles can be used in an assay of a tracer substance (Japanese Laid-Open Patent Publication Nos. 2005-283250 and 2004-325192).

In these assays, the principal reaction component is the microparticle such as latex particle or colloidal gold particle having a substance that specifically react (for example, bind) with an analyte bound thereto. The specific binding substance such as antibody present on the microparticle can bind with an analyte, thereby inducing the agglutination of microparticles. This agglutination occurs in a manner dependent on the amount of analyte, and thus a mechanical measurement of this phenomenon enables the mass of analyte to be calculated.

However, such an analyte of low molecular weight as medicaments or chemical substances has a small number of sites for binding to its specific binding substance, so that agglutination reaction is unlikely to be induced, making it difficult to construct a homogeneous measurement system using an agglutination reaction. Therefore, it has been necessary to especially add a competitor carrying a hapten bound thereto to a reaction system (see, for example, Japanese Laid-Open Patent Publication Nos. 2004-325192 and 2006-38594).

SUMMARY OF THE INVENTION

It is an object of the present invention to provide a method for measuring an analyte that has a small number of specific binding sites within the molecule using an agglutination reaction of immunological microparticles and a kit therefor.

In the present invention, using the microparticle wherein the same or an analog of the analyte and a substance that specifically binds to a substance that can specifically bind to the analyte are both bound to an insoluble carrier, and therefore it becomes to conveniently carry out the assay without especially inducing simultaneous competition of the competitor carrying hapten bound thereto and the analyte.

The present invention provides a method for measuring an analyte present in a sample, comprising:
(a) mixing the analyte, a first specific binding substance and microparticles, wherein the first specific binding substance is a substance that can specifically bind to the analyte, each of the microparticles is an insoluble carrier onto the surface of which both the same or an analog of the analyte and a second specific binding substance have been bound, and the second specific binding substance is a substance that can specifically bind to the first specific binding substance; and
(b) measuring an agglutination reaction of the microparticles in the mixture obtained in the step (a).

In one embodiment, the analyte is a hapten and the analog of the analyte is a hapten-bound protein.

In one embodiment, the substance that can specifically bind to the analyte is an antibody against the analyte.

In a certain embodiment, the second specific binding substance is a monoclonal antibody against the first specific binding substance.

In a further embodiment, the analog of the analyte is a recognition site that can bind with the substance that can specifically bind to the analyte, or a structural analog of the recognition site. Alternatively, the analog of the analyte may be a substance to which a plurality of the recognition sites or the structural analogs are bound.

In one embodiment, the insoluble carrier is latex or gold colloid.

The present invention also provides a reagent kit for assay, comprising:
a first reagent containing a first specific binding substance that is a substance that can specifically binds to an analyte; and
a second reagent containing microparticles, wherein the microparticles is an insoluble carrier onto the surface of which both the same or an analog of the analyte and a second specific binding substance have been bound, and the second specific binding substance is a substance that can specifically bind to the first specific binding substance.

In one embodiment, the analyte is a hapten and the analog of the analyte is a hapten-bound protein.

According to the present invention, it is possible to construct a homogeneous assay using an agglutination reaction in a more convenient manner, by the use of the microparticle composed of an insoluble carrier such as latex or gold colloid to which both an analyte or an analog of the analyte and a substance that specifically binds to a substance that can specifically bind to the analyte have been bound as the principal component of the agglutination reaction, without especially adding a competitor carrying hapten bound thereto to a reaction system so as to induce simultaneous competition of an analyte and the competitor.

BEST MODE FOR CARRYING OUT THE INVENTION

Figure 1:
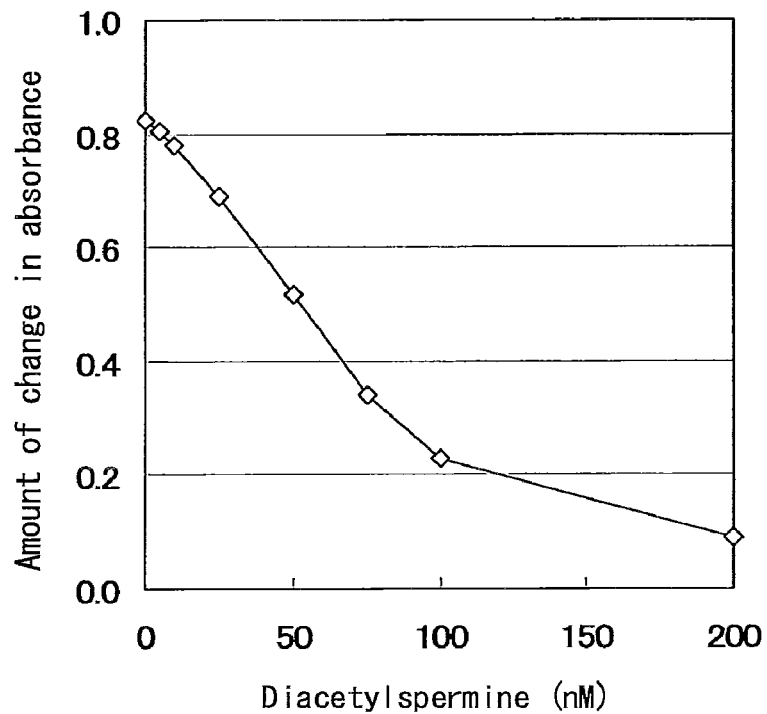
FIG. 1 is a graph showing the relationship between the concentration of diacetylspermine and the amount of change in absorbance in a diacetylspermine assay (Example 4)

In the present invention, examples of samples containing an analyte used in an assay include biological samples such as blood, plasma, serum, urine, feces (in suspension), cerebrospinal fluid, and ascites fluid; and those collected from the environment or extracts thereof.

The analyte is not particularly limited as long as a substance (the first specific binding substance) that specifically binds to the analyte can exist. Examples of the analyte include proteins such as albumin, hemoglobin, hemoglobin A1c, myoglobin, transferrin, lactoferrin, cystatin C, ferritin, α-fetoprotein, carcinoembryonic antigen, CA19-9, prostate-specific antigen, C-reactive protein (CRP), fibrin degradation product (FDP), pepsinogens I and II, and collagen; lipoproteins such as high-density lipoprotein, low-density lipoprotein, and very low-density lipoprotein; nucleic acids such as deoxyribonucleic acid and ribonucleic acid; enzymes such as alkaline phosphatase, lactate dehydrogenase, lipase, and amylase; immunoglobulins such as IgG, IgM, IgA, IgD, and IgE; antigens and antibodies associated with infectious diseases, such as hepatitis B virus, hepatitis C virus, human immunodeficiency virus, and *Helicobacter pylori* and antibodies thereto; polyamine, such as spermine, spermidine, putrescine and diacetylspermine, and physiologically active substance; drugs such as haloperidol and bromperidol; and hormones such as sex hormone.

An example of the substance (the first specific binding substance) that specifically binds to the analyte is an antibody or an antigen that can be used in an immunoassay using an immune reaction. For example, substances having binding affinity, such as antibodies or antigens, receptors, lectin, deoxyribonucleic acid (DNA), and ribonucleic acid (RNA), can be used. Preferably, a polyclonal antibody or a monoclonal antibody against the first binding substance is used in view of the ability to specifically recognize the analyte and be easily recognized by (ie, specifically bind to) the second specific binding substance which have been bound to an insoluble carrier as described in detail below. Further, a recognision site by the second specific binding substance (e.g., a tag) may be added to the first specific binding substance using a chemical or molecular biological technique. Such a first specific binding substance may be commercially available or may be prepared by a method commonly used by those skilled in the art in accordance with the analyte.

The substance (the second specific binding substance) that specifically binds to the substance (the first specifically hinging substance) that specifically binds to the analyte is bound onto the surface of an insoluble carrier. An example of the second specific binding substance is an antibody or an antigen that can be used in an immunoassay utilizing an immune reaction. Alternatively, a substance that specifically binds to a substance that specifically binds to the target to be measured can also be used. For example, substances having binding affinity, such as antibodies or antigens, receptors, lectin, deoxyribonucleic acid (DNA), and ribonucleic acid (RNA), can be used.

The second specific binding substance specifically binds to the first specific binding substance, and the binding site thereof may recognize any region present in the first specific binding substance. For example, when the first specific binding substance is an antibody, the region may be the Fc region or the V region of the antibody or a tag region or the like added to the antibody using a chemical or molecular biological technique. When the second specific binding substance is an antibody, the second specific binding substance may be a polyclonal antibody or may be a monoclonal antibody. Such a second specific binding substance may be commercially available or may be prepared by a method commonly used by those skilled in the art in depending on the first specific binding substance.

An analyte or an analog of the analyte that is bound to an insoluble carrier together with the second specific binding substance may be any substance insofar as it specifically binds to the first specific binding substance, including the same of the analyte itself, a recognition site of the analyte that is recognized by the first specific binding substance (i.e., a portion of an analyte), or a structural analog thereof. Alternatively, it may be a substance to which a plurality of such analytes or analogs are bound. When the analyte is a hapten (such as, a small molecule having a molecular weight of several hundred or less), which lacks immunogenicity and only has reactogenicity, the analog of the analyte is preferably a hapten-bound protein. Proteins for which a plurality of analytes (such as, haptens), portions thereof, or structural analogs thereof are bound are appropriately selected from albumins, hemocyanins, thyroglobulins, fibrinogens, enzymes, and the like from various animal. Bovine serum albumin (BSA) is preferable according to the present invention. As for the hapten-bound protein, it is preferable that about 4 to 40 of analytes (haptens) or portions thereof, or structural analogs thereof are bound per protein molecule.

The binding between the analytes or portions thereof and the protein can be made by a method commonly used by those skilled in the art. As an example of the binding, the analytes or portions thereof is chemically linked with a carrier directly or via a linking agent, by using a functional group, such as an amino group, a carboxyl group, or a thiol group, that is present in the analytes or portions thereof. Depending on the structure of the analytes or portions thereof, various methods are known (Laboratory Techniques in Biochemistry and Molecular Biology (Seikagaku Jikken Hou) 11, Enzyme Immunoassay, written by P. Tijssen, edited by Eiji Ishikawa, p. 252, 1989, Tokyo Kagaku Dozin Co., Ltd.). Examples of a reagent for forming a chemical linkage include an acylating agents and an alkylating agents. Preferably, N-hydroxysuccinimido ester which can be obtained by activating a carboxyl group, maleimides which can be used under weakly alkaline conditions, or the like is used.

According to the present invention, the insoluble carrier to which the analyte or an analog of the analyte and a second specific binding substance are both bound can be any microparticles that can be used for an immunoassay reagent. Latex and metal colloid are preferably used. In the case of metal colloid, gold colloid is preferable in view of generally ease to use. Commercially available colloidal gold particles may be used, or colloidal gold particles may be prepared by a method commonly used by those skilled in the art (e.g., a method of reducing chloroauric acid with sodium citrate). The particle size of the colloidal gold particles is usually in the range of 10 nm to 100 nm, preferably in the range of 30 nm to 60 nm.

The colloidal gold particles (hereinafter sometimes referred to as the bound colloidal gold particles) having both the analyte or an analog of the analyte and a second specific binding substance bound used in the method of the present invention can be prepared, for example, in the following manner. First, usually 0.01 mg to 100 mg, preferably 0.1 mg to 10 mg, of the analyte or an analog of the analyte (e.g., bovine serum albumin-bound analyte) and 0.01 mg to 100 mg, preferably 0.1 mg to 10 mg, of the second specific binding substance (e.g., an antibody) are added to 1 L of a colloidal solution containing gold particles (having an absorbance at 540 nm of about 2.0), and they are mixed with stirring under refrigeration or at room temperature for 5 minutes to 24 hours. Then, the mixture is subjected to blocking with bovine serum albumin (BSA) or the like and centrifuged, and thus the desired bound colloidal gold particles can be obtained. The obtained microparticles are dispersed in a buffer solution to attain a concentration required for assay. The pH of the buffer solution is preferably 5 to 9, and the concentration thereof is preferably 1 to 100 mM. For example, a phosphate buffer solution, a Tris-HCl buffer solution, a succinate buffer solution, or a Good's buffer solution such as glycylglycine, MES (2-(N-morpholino)ethanesulfonic acid), HEPES (2-[4-(2-hydroxyethyl)-1-piperazinyl]-ethanesulfonic acid), TES (N-tris (hydroxymethyl)methyl-2-aminoethanesulfonic acid), MOPS (3-(N-morpholino)propanesulfonic acid), PIPES (piperazine-1,4-bis(2-ethanesulfonic acid)), or Bis-Tris(bis (2-hydroxyethyl)iminotris(hydroxymethyl)methane) is preferably used as the buffer solution.

The buffer solution may contain additives, for example, sugars and sugar alcohols, sodium azide, albumin, salts such as sodium chloride, and antiseptics, as necessary. Examples of the sugars and sugar alcohols include glucose, mannose, saccharose, lactose, maltose, mannitol, and sorbitol. The concentration thereof is preferably 0.01 to 10 w/v %. As for the albumin, bovine serum albumin (BSA) is preferably used, and the concentration thereof is preferably 0.001 to 1 w/v %. As for the antiseptics, sodium azide is preferably used, and the concentration thereof is preferably 0.01 to 0.5 w/v %. Examples of other additives include Tween 20, polyethylene glycol lauryl ether, 5-bromosalicylic acid, sodium salicylate, sodium benzoate, sodium benzenesulfonate, phenol, and thymol.

For the binding reaction between the analyte and the first specific binding substance and the agglutination reaction between the resulting binding and the insoluble carrier to which the second specific binding substance and the like have been bound, reaction conditions such as reaction temperature, pH, type of the buffer solution, type and concentration of the coexistent salt, and other coexistent substances are the same as those in conventional immunological reactions. For example, in order to accelerate the reactions, a water-soluble polymer such as polyethylene glycol, polyvinyl alcohol, dextran, or sodium chondroitin sulfate may be added to the reaction system, as is commonly performed. For example, polyethylene glycol is added, depending on the measurement system, in a proportion of about 1 to 5 w/v %.

According the present invention, a method for measuring an analyte present in a sample, comprising:

(a) mixing the analyte, a first specific binding substance and microparticles, wherein the first specific binding substance is a substance that can specifically bind to the analyte, each of the microparticles is an insoluble carrier onto the surface of which both the same or an analog of the analyte and a second specific binding substance have been bound, and the second specific binding substance is a substance that can specifically bind to the first specific binding substance; and (b) measuring an agglutination reaction of the microparticles in the mixture obtained in the step (a).

In this method, in the case of the analyte can bind a plurality of first specific binding substances, in the step (a), the analyte is first reacted with the substance (the first specific binding substance) that specifically binds to the analyte to form a complex, and the complex is then reacted with the microparticle composed of an insoluble carrier such as latex or gold colloid having the substance (the second specific binding substance) that recognizes the substance that specifically binds to the analyte bound thereto, thereby causing an agglutination reaction; and in the step (b), the extent of the agglutination reaction is mechanically measured.

For example, the method of the present invention is performed in the following manner: a sample containing an analyte or a dilution of the sample appropriately diluted with a buffer or the like is mixed with a first specific binding substance that specifically binds to the analyte, for the first reaction. Subsequently, to the mixture, the microparticle composed of an insoluble carrier as obtained above are added and are mixed, for the second reaction. A first specific binding substance that is not bound to the analyte in the first reaction binds to an analyte or an analyte analog present on the insoluble carrier. A second specific binding substance present on the insoluble carrier binds to a first specific binding substance bound to the analyte or the analyte analog present on the insoluble carrier, thereby causing an agglutination reaction of the microparticles. The agglutination reaction depends on the amount of the first specific binding substance bound to the analyte present on the insoluble carrier in the second reaction, and hence it depends on the amount of the first specific binding substance that is not bound to the analyte in the first reaction. That is, the agglutination reaction of the second reaction is decreased depending on the amount of the analyte in the first reaction. For example, when gold colloid is used as the insoluble carrier, a change in absorbance at a predetermined wavelength due to the agglutination reaction is determined. The amount of the analyte in the sample can be easily found by applying the results of the determination to a calibration curve created beforehand. The calibration curve represents the relationship between the change in the absorbance due to the colloidal gold agglutination reaction and the amount of the analyte. It should be noted that, for example, a qualitative analysis and a semi-quantitative analysis can also be performed, in which the sample is determined as negative when the change in the absorbance is less than a certain value and as positive when the change in the absorbance is not less than the certain value.

When gold colloid is used, both a single wavelength measurement and a dual wavelength measurement may be used to determine the change in the absorbance after the start of the reaction. When the dual wavelength measurement is used, the change in the absorbance is determined at the first wavelength of 610 nm to 800 nm, preferably 630 nm to 750 nm, and the second wavelength of 360 nm to 580 nm, preferably 500 nm to 550 nm. When the single wavelength measurement is used, the change in the absorbance can be determined at a wavelength within the wavelength region of either one of the first wavelength or the second wavelength used in the above-described dual wavelength measurement. In the method of the present invention, the change in the absorbance refers to values obtained by either of the two measurement methods described below:

(1) the absorbance of the reaction liquid is measured twice at an appropriate interval after the start of the reaction, and the difference between the two measured values is used as the change in the absorbance; or (2) the absorbance of the reaction liquid is continuously measured after the start of the reaction, and the rate of change in the absorbance per unit time (in some cases, the maximum rate of change) is used as the change in the absorbance.

A spectrophotometer, a microplate reader, a biochemical automatic analyzer, and the like can be used in the above-described measurement. In particular, a number of samples can be determined in a short period of time by applying the method of the present invention to the measurement with the biochemical automatic analyzer.

According to the present invention, a reagent kit for assay for use with the method of the present invention is provided. The kit contains a first reagent containing a first specific binding substance that is a substance that can specifically binds to an analyte; and a second reagent containing microparticles, wherein the microparticles is an insoluble carrier onto the surface of which both the same or an analog of the analyte and a second specific binding substance have been bound, and the second specific binding substance is a substance that can specifically bind to the first specific binding substance.

The above described reagents may be provided in any form, and preferably are provided in the form where the reagents are individually sealed and packaged. The above-described kit may include a reference standard of the analyte for use in creation of a calibration curve, a buffer solution in which each substance is dissolved on use to prepare a solution having an appropriate concentration, instructions for use, and the like.

EXAMPLES

Hereinafter, the present invention will be described even more specifically by way of examples. However, it is to be understood that the present invention is not limited by the examples.

Example 1

Preparation of Colloidal Gold Solution

First, 2 mL of a 10 w/v % chloroauric acid solution was added to 1 L of distilled water at 95° C. under stirring, and after one minute, 10 mL of a 2 w/v % sodium citrate solution was added thereto, and resulting mixture was stirred for further 20 minutes, and then cooled to 30° C. After cooling, the pH was adjusted to 7.1 with 0.1 w/v % potassium carbonate.

Example 2

Preparation of Diacetylspermine and Rat Anti-Mouse IgG Monoclonal Antibody-Bound Colloidal Gold Reagent Diacetylspermine-bound BSA (see Japanese Laid-Open Patent Publication No. 2006-38594) was diluted with 10 mM HEPES (pH 7.1) containing 0.05 w/v % of sodium azide to give a solution having diacetylspermine-bound BSA at a concentration of 0.1 mg/mL. Separately, a rat anti-mouse IgG monoclonal antibody (Production of Antibodies, Reagents for Immunology and Services) was diluted with 10 mM HEPES (pH 7.1) containing 0.05 w/v % of sodium azide to give a solution having monoclonal antibody at a concentration of 40 μg/mL. Then, 50 mL of the diacetylspermine-bound BSA solution was added to about 1 L of the colloidal gold solution prepared in Example 1 above and stirring was performed for 10 minutes at room temperature, and 50 mL of the monoclonal antibody solution was then added and stirring was performed under refrigeration for 18 hours. To this solution, 110 mL of 10 mM HEPES (pH 7.1) containing 5.46 w/v % of mannitol, 0.5 w/v % of BSA, and 0.05 w/v % of sodium azide was added, and stirring was performed at room temperature for 1 hour. Centrifugation was performed at 8000 rpm for 40 minutes to remove the supernatant. About 1 L of 5 mM HEPES (pH 7.5) containing 3 w/v % of mannitol, 0.1 w/v % of BSA, and 0.05 w/v % of sodium azide (solution A) was then added to the precipitated residue to disperse the antibody-bound gold colloid. Thereafter, centrifugation was performed at 8000 rpm for 40 minutes to remove the supernatant. Then, solution A was added to disperse the antibody-bound gold colloid so that the total amount of resulting solution was 70 mL. Thus, a diacetylspermine and rat anti-mouse IgG monoclonal antibody-bound colloidal gold solution was prepared.

Then, 280 mL of solution A was added to 70 mL of the resulting diacetylspermine and rat anti-mouse IgG monoclonal antibody-bound colloidal gold solution to prepare a diacetylspermine and rat anti-mouse IgG monoclonal antibody-bound colloidal gold reagent.

Example 3

Preparation of First Reagent for Diacetylspermine Assay 1

To a solution of 0.2 M PIPES (pH 6.5) containing 1.0 w/v % of sodium chloride, 0.5 w/v % of EDTA, and 0.35 w/v % of polyoxyethylene lauryl ether (Solution B) 0.5 μg/mL of a mouse anti-diacetylspermine IgG antibody (Trans Genic Inc.) and 2.0 w/v % of polyethylene glycol as a reaction accelerator were added to give a first reagent for diacetylspermine.

Example 4

Diacetylspermine Assay 1

In this example, the first reagent for diacetylspermine assay 1 prepared in Example 3 was used as a first reagent, and the diacetylspermine and rat anti-mouse IgG monoclonal antibody-bound colloidal gold reagent prepared in Example 2 was used as a second reagent. Samples were prepared so as to have diacetylspermine at the respective concentrations of 0, 5, 10, 25, 50, 75, 100, and 200 nM. Then, 160 μL of the first reagent was added to 10 μL of a diacetylspermine-containing sample and heating was performed at 37° C. for about 5 minutes, and 80 μL of the second reagent was added for reaction at 37° C. The amount of change in absorbance was measured by a Hitachi 7070 automatic analyzer at photometric points from 18 to 31 at wavelengths of 546 nm and 660 nm. FIG. 1 and Table 1 show the relationship between the diacetylspermine concentration and the amount of change in absorbance.

TABLE 1

| Diacetylspermine (nM) | Amount of change in absorbance |
|---|---|
| 0 | 0.8245 |
| 5 | 0.8065 |
| 10 | 0.7796 |
| 25 | 0.6899 |
| 50 | 0.5172 |
| 75 | 0.3411 |
| 100 | 0.2296 |
| 200 | 0.0889 |

As shown in FIG. 1 and Table 1, the amount of change in absorbance due to an agglutination reaction was changed in a manner dependent on the concentration of analyte diacetylspermine. That is, the higher the concentration of diacetylspermine become, the lower the amount of change in absorbance become. Accordingly, it can be understood that the amount of diacetylspermine, which is the analyte present in a sample, can be quantified by measuring the amount of change in absorbance due to the agglutination reaction and comparing it to a calibration curve.

Example 5

Preparation of Second Reagent for Diacetylspermine Assay 2

To a solution of 0.2 M PIPES (pH 6.5) containing 1.0 w/v % of sodium chloride, 0.5 w/v % of EDTA, and 0.35 w/v % of polyoxyethylene lauryl ether (Solution B) 0.75 µg/mL of a mouse anti-diacetylspermine IgG antibody (Trans Genic Inc.) and 2.0 w/v % of polyethylene glycol as a reaction accelerator were added to give a second reagent for diacetylspermine assay 2.

Example 6

Diacetylspermine Assay 2

Figure 2:
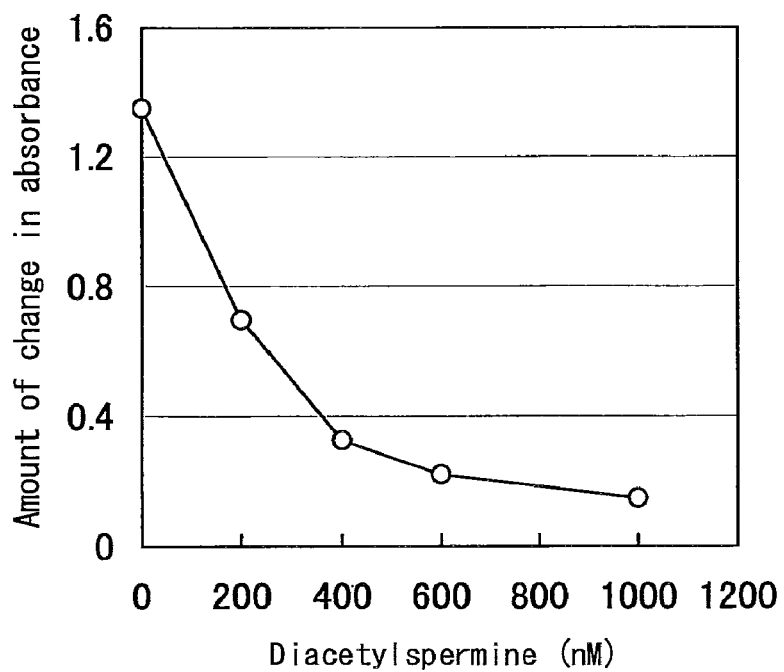
FIG. 2 is a graph showing the relationship between the concentration of diacetylspermine and the amount of change in absorbance in a diacetylspermine assay (Example 6)

In this example, the diacetylspermine and rat anti-mouse IgG monoclonal antibody-bound colloidal gold reagent prepared in Example 2 was used as a first reagent, and the second reagent for diacetylspermine assay 2 prepared in Example 5 was used as a second reagent. Samples were prepared so as to have diacetylspermine at the respective concentrations of 0, 200, 400, 600, and 1000 nM. Then, 80 µL of the first reagent was added to 10 µL of a diacetylspermine-containing sample and heating was performed at 37° C. for about 5 minutes, and 160 µL of the second reagent was added for reaction at 37° C. The amount of change in absorbance was measured by a Hitachi 7070 automatic analyzer at photometric points from 18 to 31 at wavelengths of 546 nm and 660 nm. FIG. 2 and Table 2 show the relationship between the diacetylspermine concentration and the amount of change in absorbance.

TABLE 2

| Diacetylspermine (nM) | Amount of change in absorbance |
|---|---|
| 0 | 1.3497 |
| 200 | 0.6966 |
| 400 | 0.3265 |
| 600 | 0.2204 |
| 1000 | 0.1486 |

As shown in FIG. 2 and Table 2, the amount of change in absorbance due to an agglutination reaction was changed in a manner dependent on the concentration of analyte diacetylspermine. That is, the higher the concentration of diacetylspermine, the lower the amount of change in absorbance. Accordingly, it can be understood that the amount of diacetylspermine, which is the analyte present in a sample, can be quantified by measuring the amount of change in absorbance due to the agglutination reaction and comparing it to a calibration curve.

Example 7

Preparation of Bromperidol and Mouse Anti-Rabbit IgG-Fc Monoclonal Antibody-Bound Colloidal Gold Reagent Bromperidol-bound BSA (see Japanese Laid-Open Patent Publication No. 2004-325192) was diluted with 10 mM HEPES (pH 7.1) containing 0.05 w/v % of sodium azide to give a solution having bromperidol-bound BSA at a concentration of 0.1 mg/mL. Separately, a mouse anti-rabbit IgG-Fc monoclonal antibody (Biogenesis) was diluted with 10 mM HEPES (pH 7.1) containing 0.05 w/v % of sodium azide to give a solution having monoclonal antibody at a concentration of 40 µg/mL. Then, 50 mL of the bromperidol-bound BSA solution was added to about 1 L of the colloidal gold solution prepared in Example 1 above and stirring was performed for 10 minutes at room temperature, and 50 mL of the monoclonal antibody solution was then added and stirring was performed under refrigeration for 18 hours. To this solution, 110 mL of 10 mM HEPES (pH 7.1) containing 5.46 w/v % of mannitol, 0.5 w/v % of BSA, and 0.05 w/v % of sodium azide was added, and stirring was performed for 1 hour at room temperature. Centrifugation was performed at 8000 rpm for 40 minutes to remove the supernatant. About 1 L of solution A was then added to the precipitated residue to disperse the antibody-bound gold colloid. Thereafter, centrifugation was performed at 8000 rpm for 40 minutes to remove the supernatant. Then, solution A was added to disperse the bromperidol and antibody-bound gold colloid so that the total amount of resulting solution was 70 mL. Thus, a bromperidol and mouse anti-rabbit IgG-Fc monoclonal antibody-bound colloidal gold solution reagent was prepared.

Then, 280 mL of solution A was added to 70 mL of the bromperidol and mouse anti-rabbit IgG-Fc monoclonal antibody-bound colloidal gold solution to prepare a bromperidol and mouse anti-rabbit IgG-Fc monoclonal antibody-bound colloidal gold reagent.

Example 8

Preparation of First Reagent for Bromperidol Assay

To solution B as described in Example 3 above 6 µg/mL of a rabbit anti-bromperidol polyclonal antibody (see Japanese Laid-Open Patent Publication No. 2004-325192), 4 µg/mL of a rabbit IgG negative control (Dako), and 4.5 w/v % of polyethylene glycol as a reaction accelerator were added to give a first reagent for bromperidol assay.

Example 9

Bromperidol Assay

Figure 3:
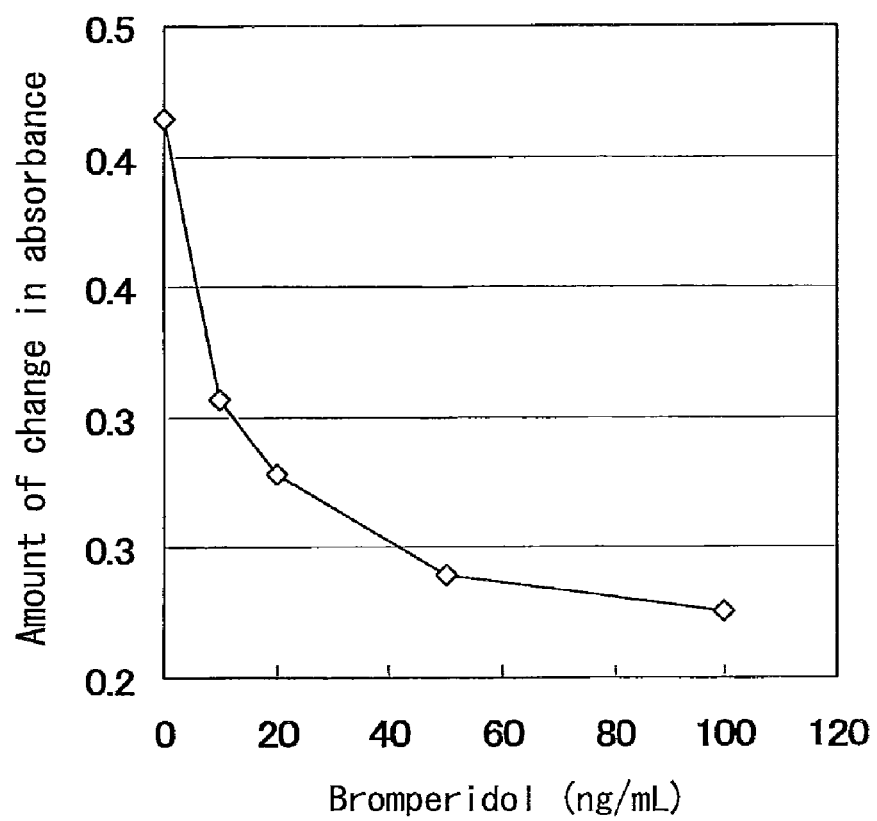
FIG. 3 is a graph showing the relationship between the concentration of bromperidol and the amount of change in absorbance in bromperidol (Example 9).

In this example, the first reagent for bromperidol assay prepared in Example 8 was used as a first reagent, and the bromperidol and mouse anti-rabbit IgG-Fc monoclonal antibody-bound colloidal gold reagent prepared in Example 7 was used as a second reagent. Bromperidol was dissolved in a 0.05M HEPES solution (pH 7.4) containing 3 w/v % bovine serum albumin at the respective concentrations of 0, 10, 20, 50, and 100 ng/mL to give samples. Then, 160 µL of the first reagent was added to 20 µL of a bromperidol-containing sample and heating was performed at 37° C. for about 5 minutes, and 80 µL of the second reagent was added for reaction at 37° C. The amount of change in absorbance was measured by a Hitachi 7070 automatic analyzer at photometric points from 18 to 31 at wavelengths of 546 nm and 660 nm. FIG. 3 and Table 3 show the relationship between the bromperidol concentration and the amount of change in absorbance.

TABLE 3

| Bromperidol (ng/mL) | Amount of change in absorbance |
|---|---|
| 0 | 0.4142 |
| 10 | 0.3070 |
| 20 | 0.2781 |
| 50 | 0.2393 |
| 100 | 0.2258 |

As shown in FIG. 3 and Table 3, the amount of change in absorbance due to an agglutination reaction was changed in a manner dependent on the concentration of analyte bromperidol. That is, the higher the concentration of bromperidol, the lower the amount of change in absorbance. Accordingly, it can be understood that the amount of bromperidol, which is the analyte present in a sample, can be quantified by measuring it as the amount of change in absorbance due to the agglutination reaction and comparing it to a calibration curve.

According to the present invention, the use of the microparticle composed of an insoluble carrier such as latex or gold colloid to which both an analyte or an analog of the analyte and a substance that specifically binds to a substance that can specifically bind to the analyte have been bound as a principal component of an agglutination reaction enables to construct a homogeneous measurement system that uses an agglutination reaction to be constructed in a more convenient manner without especially adding a competitor carrying hapten bound thereto to a reaction system so as to induce simultaneous competition of an analyte and the competitor.

Moreover, the present invention does not require the B/F separation and is therefore also very suitable for automation. Therefore, the present invention is suitable as an immunoassay of a trace constituent using an antigen-antibody reaction for use in the industrial, environmental, and clinical laboratory test fields.

The invention claimed is:

1. A method for measuring an analyte in a sample, comprising:
   (a) mixing the sample, a first specific binding substance and microparticles,
   wherein the first specific binding substance is a substance that can specifically bind to the analyte and an analog of the analyte,
   wherein each of the microparticles comprises:
   an insoluble carrier;
   the analyte or the analog of the analyte; and
   a second specific binding substance which is a substance that can specifically bind to the first specific binding substance,
   wherein the analyte or the analog of the analyte is bound onto the surface of the insoluble carrier and the second specific binding substance is bound onto the surface of the insoluble carrier, wherein the second specific binding substance is a monoclonal antibody against the first specific binding substance; and
   (b) measuring an agglutination reaction of the microparticles in the mixture obtained in the step (a), thereby determining the amount of the analyte in the sample, wherein the extent of agglutination of the microparticles decreases with an increase in the amount of the analyte in the sample.

2. The method of claim 1, wherein the analyte is a hapten and the analog of the analyte is a hapten-bound protein.

3. The method of claim 1, wherein the first specific binding substance that can specifically bind to the analyte and the analog of the analyte is an antibody against the analyte.

4. The method of claim 1, wherein the analog of the analyte is a recognition site of the analyte or a structural analog of the recognition site of the analyte that can bind specifically with the first specific binding substance that specifically binds to the analyte, or a substance to which a plurality of the first specific binding substance can specifically bind.

5. The method of claim 1, wherein the insoluble carrier is latex or gold colloid.

6. The method of claim 2 wherein the substance that can specifically bind to the analyte is an antibody against the analyte.

7. The method of claim 2, wherein the insoluble carrier is latex or gold colloid.

8. The method of claim 3, wherein the insoluble carrier is latex or gold colloid.

9. The method of claim 4, wherein the insoluble carrier is latex or gold colloid.

* * * * *